US005653236A

United States Patent [19]

Miller

[11] Patent Number: 5,653,236

[45] Date of Patent: Aug. 5, 1997

[54] APPARATUS FOR REAL-TIME DISTRIBUTED COMPUTATION OF BEAMFORMING DELAYS IN ULTRASOUND IMAGING SYSTEM

[75] Inventor: Steven C. Miller, Pewaukee, Wis.

[73] Assignee: General Electric Company, Milwaukee, Wis.

[21] Appl. No.: 581,667

[22] Filed: Dec. 29, 1995

[51] Int. Cl.[6] .................................................. A61B 8/00

[52] U.S. Cl. .................................... 128/661.01; 73/626

[58] Field of Search ........................ 128/661.01, 660.07, 128/661.09; 73/625–626; 367/7; 364/413.25

[56] References Cited

U.S. PATENT DOCUMENTS

| | | | |
|---|---|---|---|
| 5,476,098 | 12/1995 | O'Donnell | 128/661.01 |
| 5,477,859 | 12/1995 | Engeles | 128/661.01 |
| 5,501,219 | 3/1996 | Phelps et al. | 128/660.07 |

*Primary Examiner*—Francis Jaworski

*Attorney, Agent, or Firm*—Dennis M. Flaherty; John H. Pilarski

[57] ABSTRACT

An apparatus for generating the required beamforming delays for an ultrasound imaging system with minimal hardware and software. The apparatus performs an algorithm which allows the required computations to be separated into three groups. The first group includes transducer array geometry computations which are beam independent. The second group includes a small number of beam-dependent computations which are channel independent. The final group includes the channel- and beam-dependent calculations which combine the results of the first two groups to generate the required beamforming delays. This last computation is distributed to logic and simple real-time state machines per channel. This approach reduces the required computations and takes advantage of simple parallel processing to reduce the required hardware and computational time relative to conventional beamformer designs. Beam-dependent parameters are broadcast to all channels simultaneously, where they are combined with channel parameters to provide the required delay controls.

20 Claims, 8 Drawing Sheets

APPARATUS FOR REAL-TIME DISTRIBUTED COMPUTATION OF BEAMFORMING DELAYS IN ULTRASOUND IMAGING SYSTEM

FIELD OF THE INVENTION

This invention generally relates to ultrasound imaging systems which form ultrasonic beams by time delay and summation of return signals in a multiplicity of parallel channels. In particular, the invention relates to means for providing the required beamforming delays to channel processing.

BACKGROUND OF THE INVENTION

Conventional ultrasound imaging systems comprise an array of ultrasonic transducers which are used to transmit an ultrasound beam and then receive the reflected beam from the object being studied. For ultrasound imaging, the array typically has a multiplicity of transducers arranged in a line and driven with separate voltages. By selecting the time delay (or phase) and amplitude of the applied voltages, the individual transducers can be controlled to produce ultrasonic waves which combine to form a net ultrasonic wave that travels along a preferred vector direction and is focused at a selected point along the beam. Multiple firings may be used to acquire data representing the same anatomical information. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. By changing the time delay and amplitude of the applied voltages, the beam with its focal point can be moved in a plane to scan the object.

The same principles apply when the transducer is employed to receive the reflected sound (receiver mode). The voltages produced at the receiving transducers are summed so that the net signal is indicative of the ultrasound reflected from a single focal point in the object. As with the transmission mode, this focused reception of the ultrasonic energy is achieved by imparting separate time delay (and/or phase shifts) and gains to the signal from each receiving transducer.

Such scanning comprises a series of measurements in which the steered ultrasonic wave is transmitted, and the reflected ultrasonic wave is received and stored. Typically, transmission and reception are steered in the same direction during each measurement to acquire data from a series of points along an acoustic beam or scan line. The receiver is dynamically focused at a succession of ranges along the scan line as the reflected ultrasonic waves are received.

An ultrasound image is composed of multiple image scan lines. A single scan line (or small localized group of scan lines) is acquired by transmitting focused ultrasound energy at a point in the region of interest, and then receiving the reflected energy over time. The focused transmit energy is referred to as a transmit beam. During the time after transmit, one or more receive beamformers coherently sum the energy received by each channel, with dynamically changing phase rotation or delays, to produce peak sensitivity along the desired scan lines at ranges proportional to the elapsed time. The resulting focused sensitivity pattern is referred to as a receive beam. A scan line's resolution is a result of the directivity of the associated transmit and receive beam pair.

Scan lines are defined by their position and angle. The intersection of a beam with the transducer face is referred to as the phase center. The angle of a scan line relative to orthogonal is referred to as the steering angle.

Beamforming delays may be fixed or dynamic. Transmit delays are fixed to provide peak pressure at a particular range. Receive delays are typically dynamic since the peak sensitivity must track the increasing range r of reflections as a function of elapsed time t:

$$r = t\frac{c}{2} \tag{1}$$

where c is the speed of sound in the imaged media. The elapsed time may be quantized by an amount τ, which is equivalent to quantized focal ranges:

$$r = n\tau\frac{c}{2} \tag{2}$$

The geometry used herein is shown in FIGS. 6A and 6B for linear/sector and curved linear transducers, respectively. The important reference points are the phase center, focal point and element position. The phase center will always be the origin of the (x,z) Cartesian coordinate system. The focal point is r and the element position is $p_i$. For curved arrays the element position is determined by the radius of curvature ρ and the channel angle $\Phi_i = l_i\rho$, where $l_i$ is the distance from phase center along the face of the probe.

The beamformer must compensate for channel to channel differences in the propagation time $T_p$ of sound traveling between phase center and $p_i$ via a reflector at r. The relative delay $T_d$ is the difference between the propagation time for channel i and the propagation time for the phase center. For the geometry in FIG. 6A, the times $T_p$ and $T_d$ are as follows:

$$T_d(x_i,\theta,r) \equiv \frac{1}{c}\left((x_i^2 + r^2 - 2x_i r\sin\theta)^{1/2} - r\right) \tag{3}$$

$$T_p(x_i,\theta,r) \equiv \frac{1}{c}\left((x_i^2 + r^2 - 2x_i r\sin\theta)^{1/2} + r\right) \tag{4}$$

$$T_d(x_i, z_i, r) \equiv \frac{1}{c}\left([x_i^2 + (r - z_i)^2]^{1/2} - r\right) \tag{5}$$

$$T_p(x_i, z_i, r) \equiv \frac{1}{c}\left([x_i^2 + (r - z_i)^2]^{1/2} + r\right) \tag{6}$$

Referring to FIG. 1, the ultrasonic imaging system incorporating the invention includes a transducer array 10 comprised of a plurality of separately driven transducer elements 12, each of which produces a burst of ultrasonic energy when energized by a pulsed waveform produced by a transmitter 22. The ultrasonic energy reflected back to transducer array 10 from the object under study is converted to an electrical signal by each receiving transducer element 12 and applied separately to a receiver 24 through a set of transmit/receive (T/R) switches 26. The T/R switches 26 are typically diodes which protect the receive electronics from the high voltages generated by the transmit electronics. The transmit signal causes the diodes to shut off or limit the signal to the receiver. Transmitter 22 and receiver 24 are operated under control of a scan controller 28 responsive to commands by a human operator. A complete scan is performed by acquiring a series of echoes in which transmitter 22 is gated ON momentarily to energize each transducer element 12, and the subsequent echo signals produced by each transducer element 12 are applied to receiver 24. A channel may begin reception while another channel is still transmitting. The receiver 24 combines the separate echo signals from each transducer element to produce a single echo signal which is used to produce a line in an image on a display monitor 30.

Transmitter 22 drives transducer array 10 such that the ultrasonic energy produced is directed, or steered, in a beam. To accomplish this, transmitter 22 imparts a time delay to the respective pulsed waveforms W. that are applied to successive transducer elements 12 via respective beamformer channels. Each channel has a respective pulser associated therewith. By adjusting the pulse time delays appropriately in a conventional manner, the ultrasonic beam can be directed away from axis 36 by an angle θ and/or focused at a fixed range R. A sector scan is performed by progressively changing the time delays in successive excitations. The angle θ is thus changed in increments to steer the transmitted beam in a succession of directions.

The echo signals produced by each burst of ultrasonic energy reflect from objects located at successive ranges along the ultrasonic beam. The echo signals are sensed separately by each transducer element 12 and the magnitude of the echo signal at a particular point in time represents the amount of reflection occurring at a specific range. Due to the differences in the propagation paths between a reflecting point P and each transducer element 12, however, these echo signals will not be detected simultaneously and their amplitudes will not be equal. Receiver 24 amplifies the separate echo signals, imparts the proper time delay to each, and sums them to provide a single echo signal which accurately indicates the total ultrasonic energy reflected from point P located at range R along the ultrasonic beam oriented at the angle θ.

To simultaneously sum the electrical signals produced by the echoes impinging on each transducer element 12, time delays are introduced into each separate beamformer channels of receiver 24. The beam time delays for reception are the same delays as the transmission delays described above. However, the time delay of each receiver channel is continuously changing during reception of the echo to provide dynamic focusing of the received beam at the range R from which the echo signal emanates.

Under the direction of scan controller 28, receiver 24 provides delays during the scan such that steering of receiver 24 tracks the direction θ of the beam steered by transmitter 22 and provides the proper delays and phase shifts to dynamically focus at points P along the beam. Thus, each transmission of an ultrasonic pulse waveform results in the acquisition of a signal with a magnitude which represents the amount of reflected sound from anatomy located along the ultrasonic beam.

A detector 25 converts the received signal to display data. In the B-mode (greyscale), this would be the envelope of the signal with some additional processing such as edge enhancement and logarithmic compression.

Scan converter/interpolator 32 receives the display data from detector 25 and converts the data into the desired image for display. In particular, the scan converter converts the acoustic image data from polar coordinate (R-θ) sector format or Cartesian coordinate linear array to appropriately scaled Cartesian coordinate display pixel data at the video rate. This scan-converted acoustic data is then output for display on display monitor 30, which images the time-varying amplitude of the envelope of the signal as a grey scale.

Referring to FIG. 2, the receiver comprises a receive beamforming section 34 and a signal processor 38. The receive beamforming section 34 of receiver 24 includes separate beamformer channels 35. Each beamformer channel 35 receives the analog echo signal from a respective transducer element. The beamformer controller 50 converts scan line and transmit focus numbers to addresses into a channel control memory 54 (see FIG. 4). The scan controller 28 (FIG. 1) and beamformer controller 50 (FIG. 2) are loaded by the system host CPU in response to user actions such as changing the display format or connecting a different ultrasound probe.

As seen in FIG. 3, each beamformer channel 35 comprises a receive channel and a transmit channel, each channel incorporating delay means 40 and 42 respectively, which are controlled to provide the needed beamforming delays by receive control logic 44 and transmit control logic 46 respectively. Transmit is typically done by using a counter to delay the start of transmit pulse generation. Some systems may also apply relative phase rotations in addition to, or in place of, delays for receive. The receive channels also have circuitry 48 for apodizing and filtering the receive pulses.

The signals entering the summer 36 (see FIG. 2) have been delayed so that when they are summed with delayed signals from each of the other beamformer channels 35, the summed signals indicate the magnitude and phase of the echo signal reflected from anatomy located along the steered beam (θ). Signal processor 38 receives the beam samples from the summer 36 and produces an output to scan converter 32 (see FIG. 1).

Referring to FIG. 4, most conventional designs for the receive or transmit channel control perform beam and channel-dependent complex computations on a single central processing unit 58 and store the results in a large channel control memory 54. The channel control memory 54 is loaded by the system host CPU 58 and receives addresses corresponding to the scan line or focus number from the beamformer controller 50. Channel control of beamforming delays is typically provided by some type of delay generator logic 56 which receives control parameters from control memory 54. The control memory must contain all the necessary control parameters associated with that channel for each beam. The total amount of memory required for a 128-channel beamformer, to produce 1024 beams, is 128×1024×N, where N is the number of control parameters. These control parameters are then transmitted to the receive control logic or the transmit control logic as needed.

SUMMARY OF THE INVENTION

The present invention is an apparatus for generating the required beamforming delays for an ultrasound imaging system with minimal hardware and software. The apparatus performs an algorithm which allows the required computations to be separated into three groups. The first group comprises transducer array geometry computations which are beam independent. The second group comprises a small number of beam-dependent computations which are channel independent. The final group comprises the channel- and beam-dependent calculations which combine the results of the first two groups to generate the required beamforming delays. This last computation is distributed to logic and simple real-time state machines per channel.

The foregoing approach dramatically reduces the required computations and takes advantage of simple parallel processing to reduce the required hardware and computational time relative to conventional beamformer designs. This invention replaces the large memories of the prior art with simple logic. Beam-dependent parameters are broadcast to all channels simultaneously, where they are combined with channel parameters to provide the required delay controls.

DETAILED DESCRIPTION OF THE PREFERRED EMBODIMENTS

Figure 1:
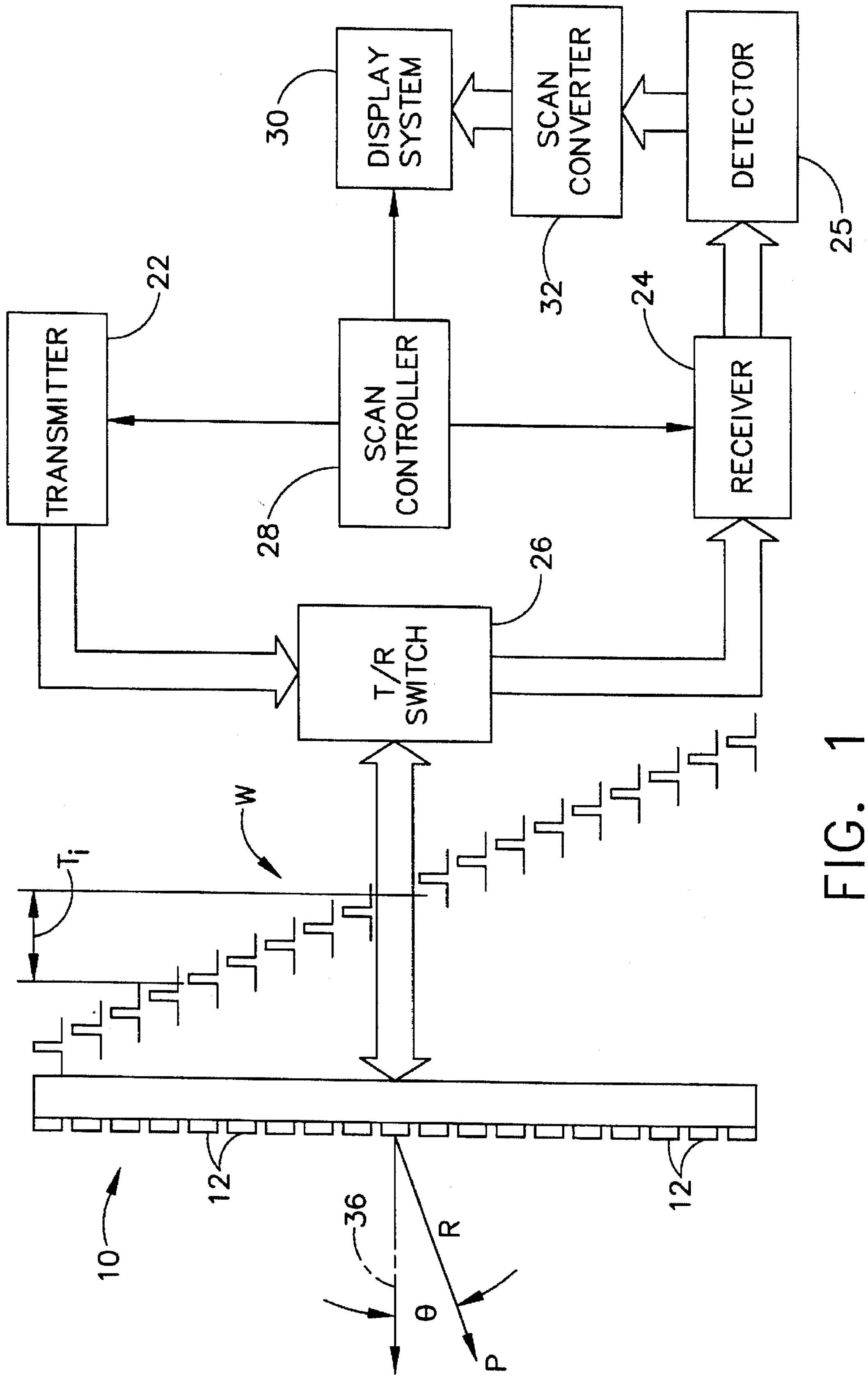
FIG. 1 (PRIOR ART)
FIG. 1 is a block diagram showing the major functional subsystems within a conventional real-time ultrasound imaging system.
Figure 2:
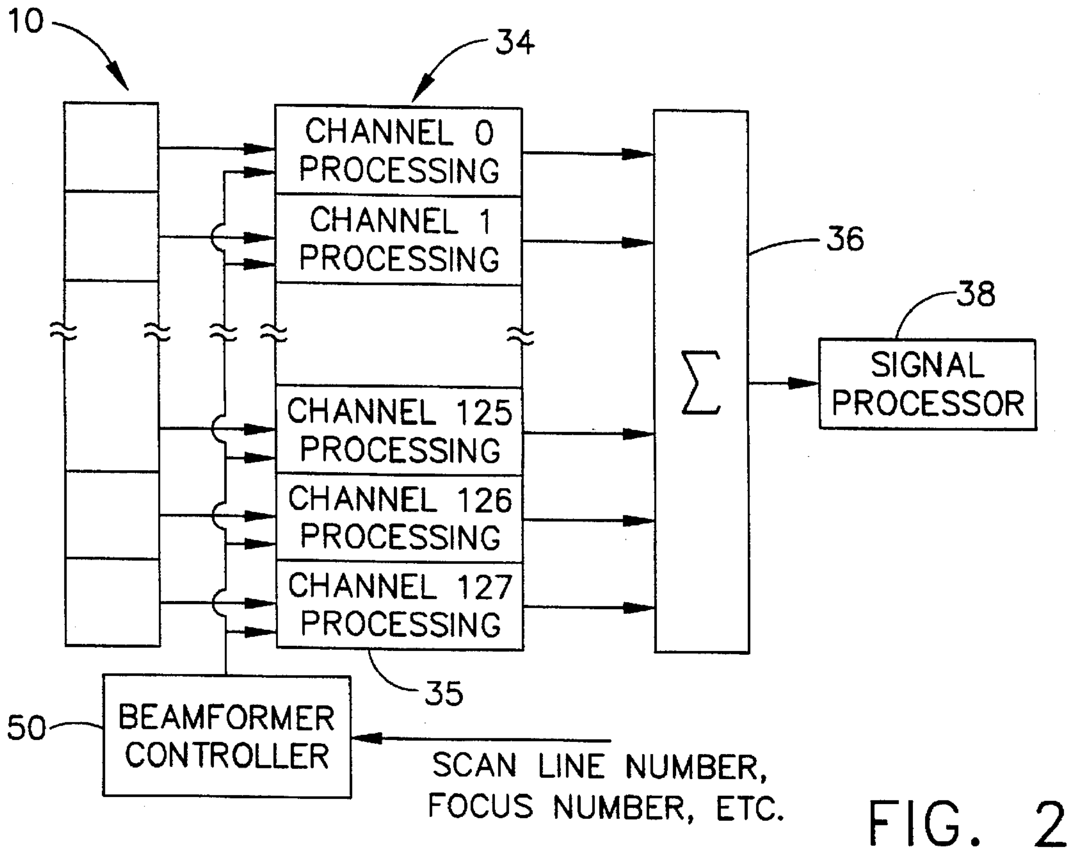
FIG. 2 (PRIOR ART)
FIG. 2 is a block diagram of a typical 128-channel beamformer for the system depicted in FIG. 1.
Figure 3:
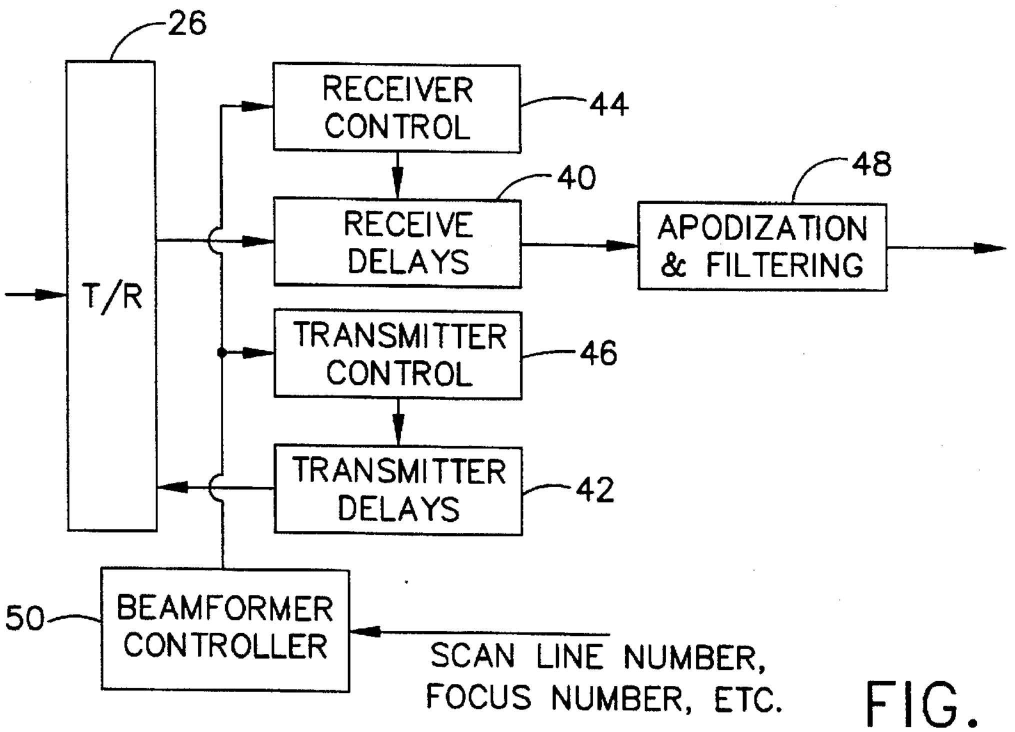
FIG. 3 (PRIOR ART)
FIG. 3 is a block diagram of the channel processing in the conventional beamformer depicted in FIG. 2.
Figure 4:
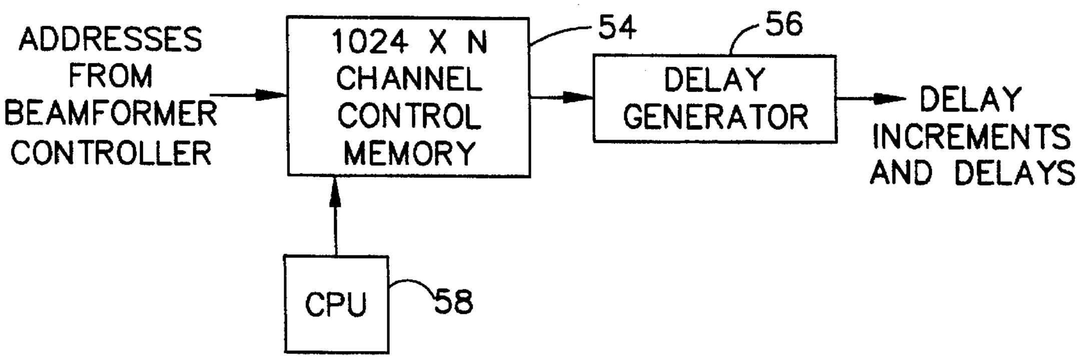
FIG. 4 (PRIOR ART)
FIG. 4 is a block diagram of a typical receive or transmit channel control for 1024 scan-lines and N control parameters.
Figure 5:
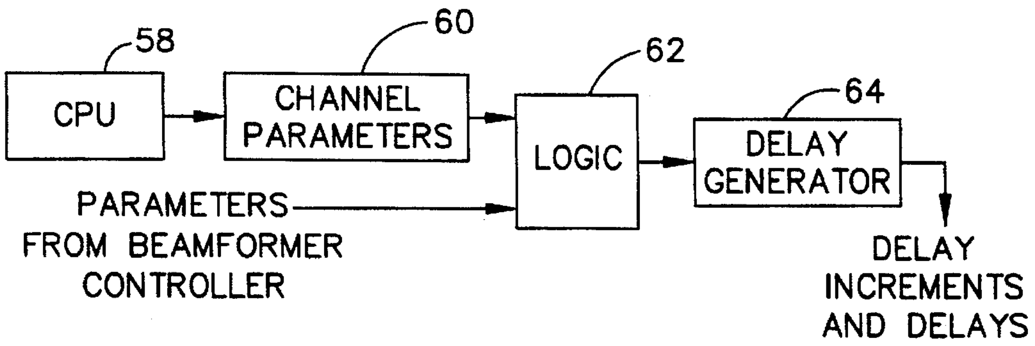
FIG. 5 is a block diagram of a receive or transmit channel control using simple logic in accordance with the present invention.
Figure 6A:
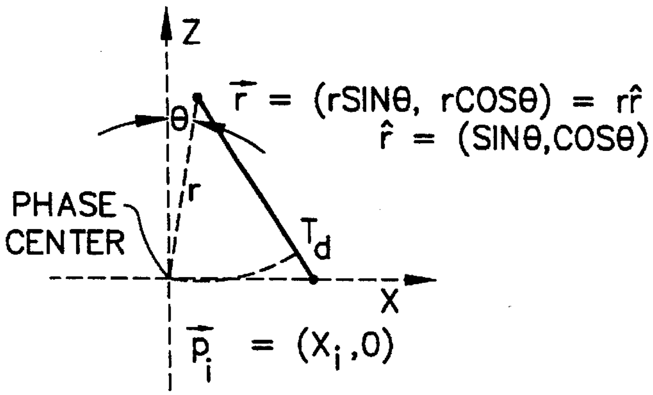
FIGS. 6A and 6B are diagrams showing the beamforming geometry for linear/sector and curved linear transducers respectively.
Figure 6B:
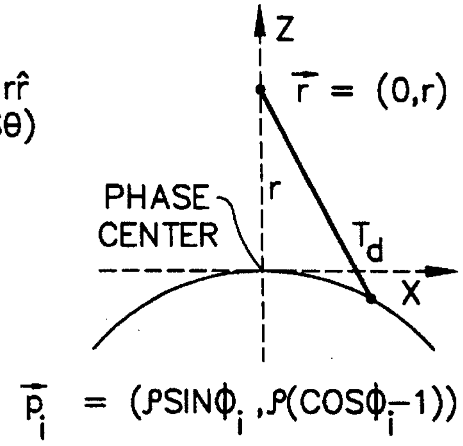

The apparatus of the present invention substitutes simple logic for the large memory required in conventional beamforming delay generation. The delay processor in accordance with the basic concept of the invention is shown in FIG. 5. The beamforming delay logic 62 combines beam-dependent parameters and channel parameters to produce control parameters needed by the delay generator 64. The delay generator 64 generates initial delays and delay increments as a function of the control parameters.

The beam-dependent parameters are broadcast to all channels simultaneously by the beamformer controller 50 before each beam during scanning. The channel parameters are stored in respective registers 60 associated with each channel. The channel parameters are loaded into registers 60 by the CPU 58 before scanning. These beam- and channel-dependent parameters are a function of the beamforming geometry.

For linear or sector arrays, a good approximation for the beamforming relative delays $T_d$ is the paraxial approximation:

$$T_d(x_i,\theta,r) \approx \frac{x_i^2\cos^2\theta}{2c(r - x_i\sin\theta)} - \frac{x_i}{c}\sin\theta \tag{7}$$

The present invention uses this approximation only to guide its development. Its final accuracy will exceed this approximation.

Normally the beamforming delay function $D(x_i,\theta,r)$ compensates for the relative propagation delay by subtracting it from a constant $T_o$ and quantizing by an amount q. The desired beamforming delay function is as follows:

$$D(x_i,\theta,r) \equiv \frac{T_0 - T_d(x_i,\theta,r)}{q} \approx \frac{T_0}{q} + \frac{x_i}{qc}\sin\theta - \frac{x_i^2\cos^2\theta}{2qc(r - x_i\sin\theta)} \tag{8}$$

If the range r is replaced by the guantized elapsed time from Eq. (2), then the approximation of Eq. (8) has the following form:

$$D(x_i,\theta,n) \approx S - \frac{F}{n-G} \tag{9}$$

The desired delay function can be divided into an initial delay J and a dynamic delay $K_n$ for each channel as follows:

$$J \equiv D(x_i,\theta,n_o) \tag{10}$$

Eq. (11) can be further simplified by defining the variables M, Δn and m as follows:

$$K_n \equiv D(x_i,\theta,n) - D(x_i,\theta,n_0) \approx \frac{F}{n_0 - G}\;\frac{n - n_0}{n - G} \tag{11}$$

$$M \equiv \frac{F}{n_0 - G} = \frac{x_i^2\cos^2\theta}{2q\left(\frac{n_0\tau}{2}c^2 - x_i c\sin\theta\right)} \tag{12}$$

$$\Delta n \equiv n - n_0 \tag{13}$$

$$m \equiv n_0 - G = n_0 - 2\frac{x_i}{c\tau}\sin\theta \tag{14}$$

The result is:

$$K_n \approx M\frac{\Delta n}{\Delta n + m} \tag{15}$$

The simple expression of Eq. (15) can be easily implemented in a very compact state machine. Ideally its output delay $P_n$ is equal to the dynamic delay function $K_n$ as follows:

$$M\frac{\Delta n}{\Delta n + m} = P_n \tag{16}$$

where the term on the left-hand side of Eq. (16) is the desired delay and the term on the right-hand side is the current output delay. Rearranging Eq. (16), we get:

$$P_n m - \Delta n(M - P_n) = 0 \tag{17}$$

When this quantity is zero, there is no error, i.e., the current output delay equals the desired delay. However, due to the inherent quantization of $P_n$, zero error is not normal; there will typically be some error. This error can be monitored using an internal variable $C_n$:

$$C_n = P_n m - \Delta n(M - P_n) \tag{18}$$

The internal variable $C_n$ can be generated as shown in Eq. (19), given two additional internal variables $A_n$ (Eq. (22)) and $B_n$ (Eq. (25)). These internal variables must be initialized as shown in Eqs. (23) and (26), and updated as shown in Eqs. (24) and (27):

$$C_{n+1} = \begin{cases} C_n - A_n & \text{if } P_{n+1} = P_n \\ C_n - A_n + B_n & \text{if } P_{n+1} = P_n + 1 \end{cases} \tag{19}$$

$$C_{n_0} = 0 \tag{20}$$

$$P_{n_0} = 0 \tag{21}$$

$$A \equiv M - P_n \tag{22}$$

$$A_{n_0} = M \tag{23}$$

$$A_{n+1} = \begin{cases} A_n & \text{if } P_{n+1} = P_n \\ A_n - 1 & \text{if } P_{n+1} = P_n + 1 \end{cases} \tag{24}$$

$$B_n \equiv m + \Delta n \tag{25}$$

-continued $$B_{n_0}=m \tag{26}$$

$$B_{n+1}=B_n+1 \tag{27}$$

An important feature of $C_n$ is that it decreases monotonically with time $\Delta n$ given no change in output delay (see Eq. (19)). This is a result of the internal variable $A_n$ in Eq. (22) always being positive. Conversely, it will always increase with an increase in the output delay. Thus, the state machine can provide a good approximation by incrementing $P_n$ whenever $C_n$ crosses 0, i.e. becomes negative.

Figure 7:
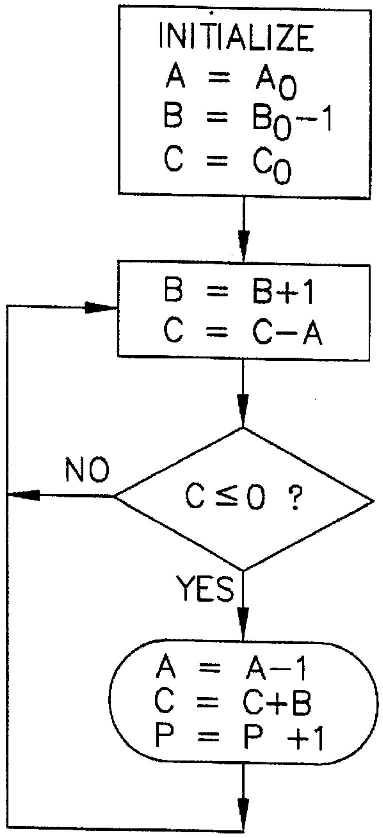
FIG. 7 is a flow diagram showing the delay generator state machine algorithm in accordance with the present invention.

The decision to increment the output dynamic delay $P_n$ is based on the computation of $C_{n+1}$ given no increment (see Eq. (19)). If $C_{n+1}$ would be negative without an incrementing of the output delay $P_n$, then $P_n$ is incremented ($P_{n+1}=P_n+1$). A flow diagram for this state machine is shown in FIG. 7.

Figure 8C:
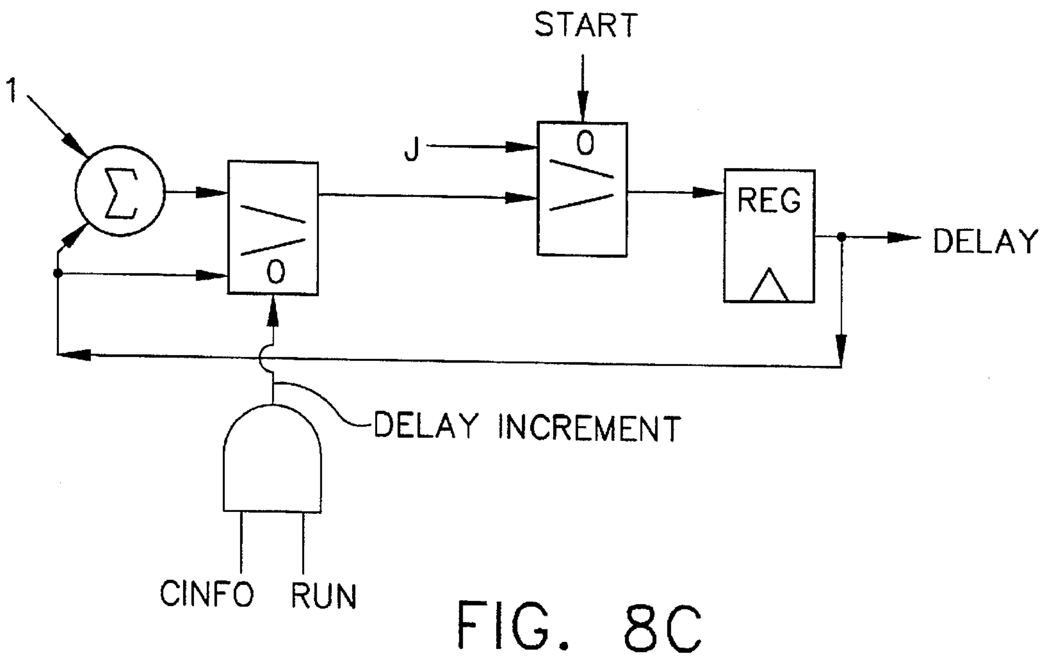
FIGS. 8A–8C are logic diagrams showing one possible implementation of a delay generator state machine comprising count-down timers (FIG. 8A), a state machine core (FIG. 8B) and a delay accumulator (FIG. 8C) in accordance with a preferred embodiment of the invention.
Figure 8A:
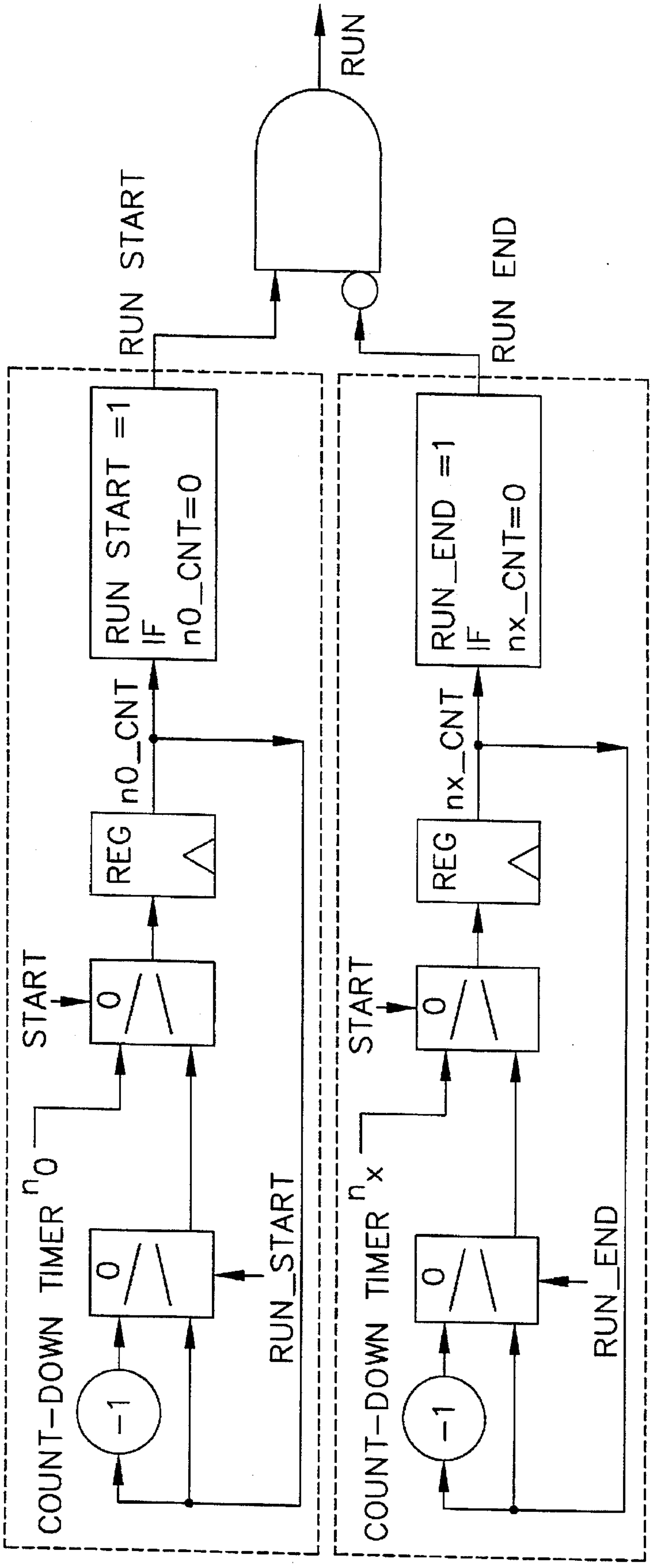
Figure 8B:
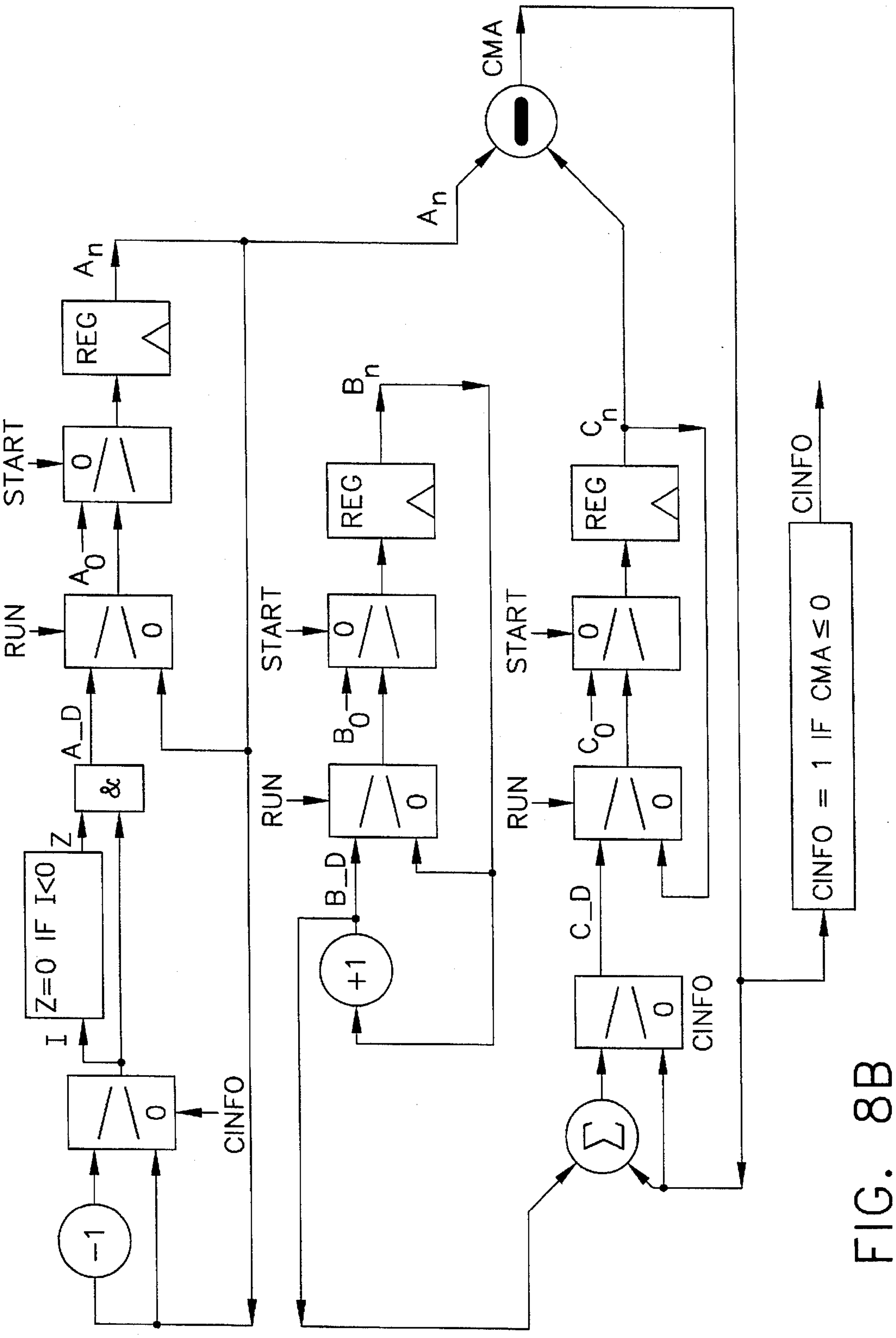
Figure 9A:
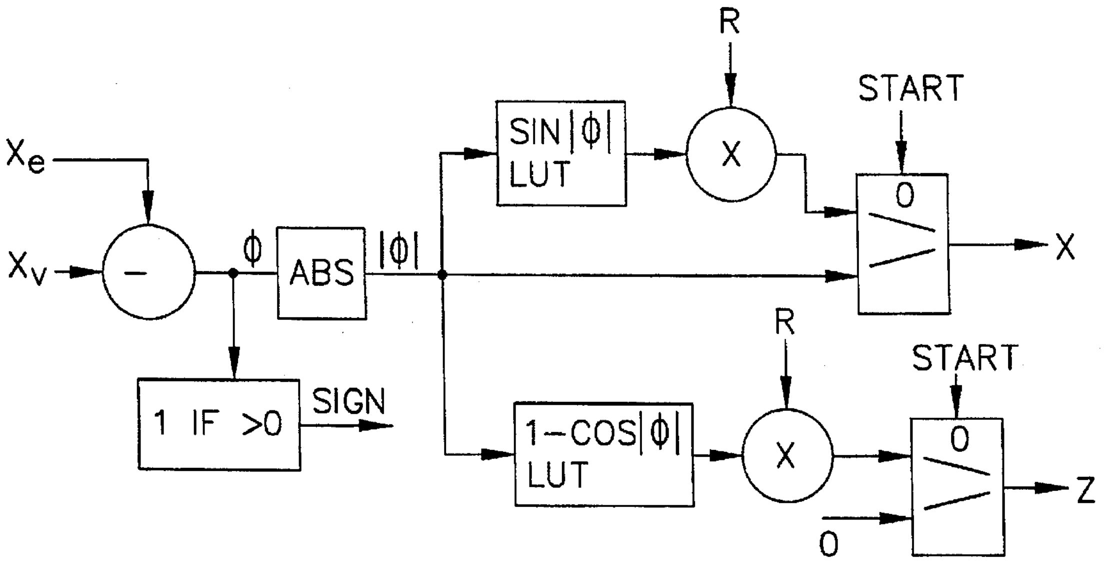
FIGS. 9A–9E are logic diagrams showing the channel logic for each transmit or receive beam in accordance with the preferred embodiment of the invention.
Figure 9B:
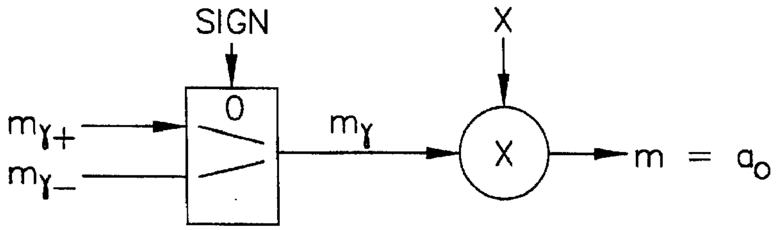
Figure 9C:
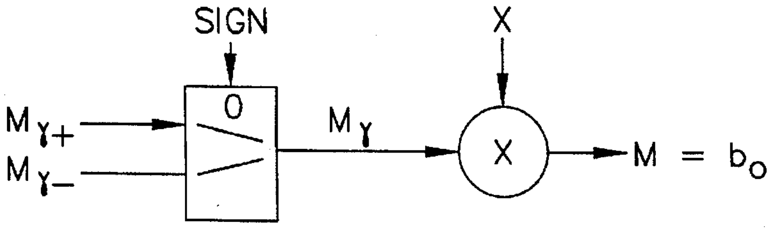
Figure 9D:
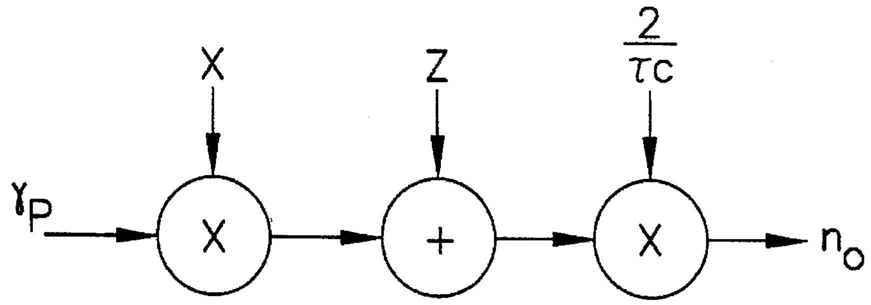
Figure 9E:
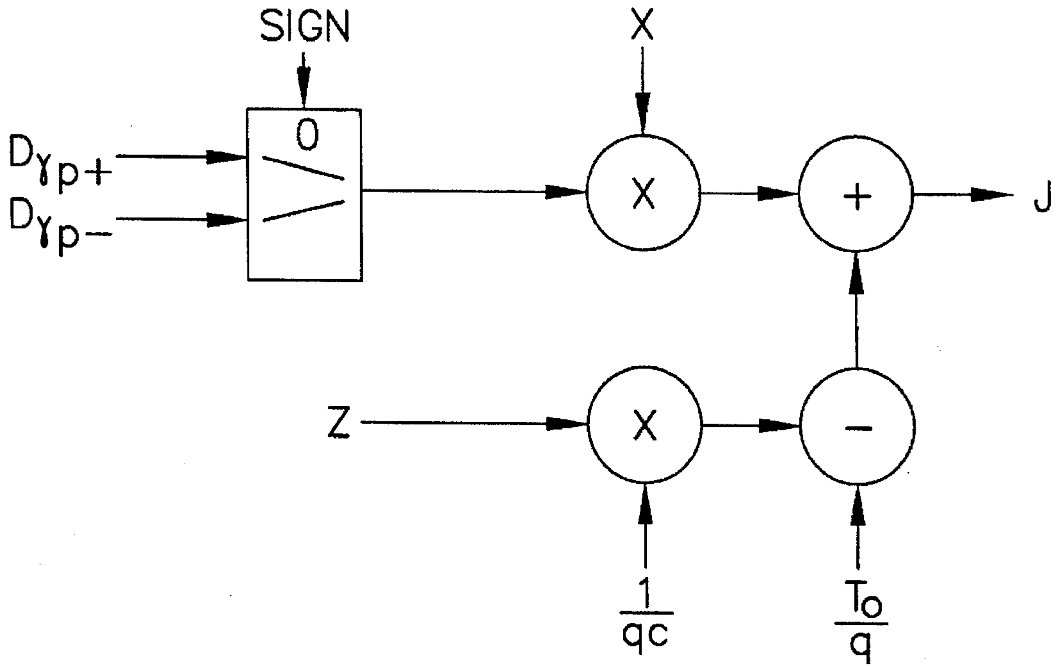

The resulting state machine can produce the paraxial approximation in real time with very little hardware. One possible implementation of the delay generator 64 (see FIG. 5) is shown in FIGS. 8A–8C. All registers are initialized with an active low "Start" pulse. FIG. 8A depicts two count-down timers to control when the state machine starts and stops running. FIG. 8B depicts a state machine core, which updates $A_n$, $B_n$ and $C_n$. FIG. 8C depicts a delay accumulator which is initialized with the static delay J and incremented when C crosses zero (CINF0=1).

With some minor modifications the state machine can produce more accurate results and compensate for initial delay (J) errors. Better accuracy is achieved by scaling up all the internal variables, and offsetting their initial values to remove biases. Initial delay errors can be accounted for by adjusting $C_0$.

To extend the delay state machine to an exact solution, the state machine and initial values given above are combined to generate a delay or phase function in the following form:

$$T_d(x_i,\theta,n)=J+M\frac{\Delta n}{\Delta n+m}\approx D(x_i,\theta,n) \tag{28}$$

Although the form of the paraxial approximation provided a starting point, more accurate and solutions can be obtained by solving the right-hand approximation in Eq. (28) exactly, at a set of points. Solving for J, M and m at three ranges $r_p$, $r_q$ and $r_r$ reduces the approximation error, over all ranges, to less than the quantization error, i.e., the algorithm is virtually exact.

General solutions for J, M and m are given in Eqs. (29), (33) and (34), respectively, where $r_p$ was picked to be equal to $r_0$, the starting range of the state machine:

$$J=D(x_i,\theta,r_p) \tag{29}$$

$$D_n\equiv D(x_i,\theta,r_n) \tag{30}$$

$$f\equiv\frac{D_r-D_q}{r_r-r_q}\ \frac{r_q-r_p}{D_q-D_p} \tag{31}$$

$$g\equiv\frac{f(r_r-r_p)}{1-f} \tag{32}$$

$$m=(r_p+g)\frac{2}{c\tau} \tag{33}$$

$$M=\frac{r_q+g}{r_q-r_p}\ (D_q-D_p) \tag{34}$$

Initialization is realized using distributed computation. By selecting the solution ranges so that they are proportional to the channel position $x_i$ as follows:

$$r_n=\gamma_n|x_i|+z_i \tag{35}$$

with proportionality constants γ which are channel independent, the computations can be distributed. All the required computations are separated into three groups.

The first group contains array geometry, channel-dependent, beam-independent computations performed by the system CPU before scanning. The results of these computations are loaded into registers 60 associated with each channel.

The second group contains beam-dependent computations which are channel independent. The results of these beam-dependent computations are broadcast to all channels during scanning by the beamformer controller 50. They can be computed by the CPU before scanning and then stored in a relatively small "beam" memory which is read during scanning. Alternatively, they can be produced real-time during scanning.

The last group of computations are extremely simple beam- and channel-dependent calculations using the results of the first two groups of computations. They are distributed, i.e., very simple logic 62 (see FIG. 5) associated with each channel performs the computations in parallel during the previous beam or during dead time between beams. This is a significant reduction in computation and hardware from conventional designs which require complex computations performed per channel and beam. Generally these "prior art" systems need to perform all of these computations prior to scanning, in the system CPU or design workstation, and store them in large memories.

There is only one channel-dependent variable: the transducer element position $x_{ci}$ relative to the array face center. The other variable which is needed for the distributed processing is the radius of curvature R. The channel-dependent variable can be stored per channel before scanning or broadcast during scanning.

Ten beam-dependent values are broadcast to all channels during scanning: $T_0/q$, $n_x$, $\gamma_p$, $x_v$, $D_{\gamma p+}$, $D_{\gamma p-}$, $m_{\gamma+}$, $m_{\gamma-}$, $M_{\gamma+}$, and $M_{\gamma-}$. $T_o$ is the delay offset to ensure positive delays; the proportionality constant $\gamma_p$ is calculated so that $r_p$ is always less than the turn-on range (as the focal range increases, channels are turned on to grow the active aperture as a function of range); $x_v$ is the beam phase center position relative to the array face center; and $n_x$, $D_{\gamma p+}$, $D_{\gamma p-}$, $m_{\gamma+}$, $m_{\gamma-}$, $M_{\gamma+}$, and $M_{\gamma-}$ are determined in accordance with Eqs. (36), (37), (42) and (43) as follows:

$$n_x\equiv\frac{1}{2\tau c} \tag{36}$$

$$D_{\gamma p\pm}\equiv D(\pm1,\theta,\gamma_p)-\frac{T_0}{q} \tag{37}$$

$$D_{\gamma q\pm}\equiv D(\pm1,\theta,\gamma_q)-\frac{T_0}{q} \tag{38}$$

$$D_{\gamma r\pm}\equiv D(\pm1,\theta,\gamma_r)-\frac{T_0}{q} \tag{39}$$

$$f_{\gamma\pm}\equiv\frac{D_{\gamma r\pm}-D_{\gamma q\pm}}{\gamma_r-\gamma_q}\ \frac{\gamma_q-\gamma_p}{D_{\gamma q\pm}-D_{\gamma p\pm}} \tag{40}$$

$$g_{\gamma\pm}\equiv\frac{f_{\gamma\pm}(\gamma_r-\gamma_p)}{1-f_{\gamma\pm}} \tag{41}$$

$$m_{\gamma\pm}\equiv(g_{\gamma\pm}+\gamma_p)\frac{2}{\tau c} \tag{42}$$

$$M_{\gamma\pm}\equiv\frac{(\gamma_q+\gamma_{m\pm})}{(\gamma_q-\gamma_p)}\ (D_{\gamma q\pm}-D_{\gamma p\pm}) \tag{43}$$

For each scan line, each channel must initialize and run the delay state machine(s) using the stored channel-dependent values and broadcast beam-dependent values.

The required initialization values per beam are J, m, M, and $n_o$, which are determined as follows:

$$J = |x_i| D_{\gamma p\,sign(x_i)} - \frac{z_i}{q} + \frac{T_0}{q} \quad (44)$$

$$m = |x_i| m_{\gamma sign(x_i)} \quad (45)$$

$$M = |x_i| M_{\gamma sign(x_i)} \quad (46)$$

$$n_0 = (|x_i| \gamma_p + z_i) \frac{2}{\tau c} \quad (47)$$

where $\Phi_i$, $x_i$ and $z_i$ are defined as follows:

$$\phi_i = x_v - x_{e_i} \quad (48)$$

$$x_i = \begin{cases} \phi_i, \text{ if } R = 0 \text{ (Linear or Sector)} \\ R \sin \phi_i, \text{ if } R \neq 0 \text{ (Convex)} \end{cases} \quad (49)$$

$$z_i = \begin{cases} 0, \text{ if } R = 0 \text{ (Linear or Sector)} \\ R (\cos \phi_i - 1), \text{ if } R \neq 0 \text{ (Convex)} \end{cases} \quad (50)$$

All the computations may be done with a small number of multiply-accumulates, with the exception of the sine and cosine required by convex probes. An example of the simple logic required is shown in FIGS. 9A–9E. These computations can be done during the scan line preceding the one for which the computation results are needed, making the computational speed requirement very slow. Dedicated logic may be used as shown, or logic may be reduced by multiplexing multipliers between computations or using a very simple microprocessor. All of this logic may be highly integrated on custom integrated circuits together with FIFOs or Cordic rotators that apply the required delay or phase rotations to the transmit and receive signals.

Separate transmit and receive state machines may be provided per channel. During the n-th scan line the receive state machine is producing delays for the n-th beam, while the transmit state machine is producing delays for the (n+1)-th beam. Simultaneously, the channel logic computes the (n+1)-th scan line receive initialization together with the (n+2)-th transmit initialization.

The foregoing preferred embodiment has been disclosed for the purpose of illustration. Variations and modifications will be readily apparent to those skilled in the art of beamforming for ultrasound imaging. The parallel distributed control architecture of the invention could be applied to any method of beamforming, including, but not limited to, analog beamformers with tap delay lines and/or phase rotations using intermediate frequency mixers or baseband demodulators (phase rotation is often used as an approximation to time delay for relatively narrow bandwidth signals), digital beamformers using FIFOs and/or cordic rotators, demodulators or intermediate frequency mixers, for phase rotation. As used in the claims, the term "delay" includes time delay, tap delay or phase rotation. Furthermore, in accordance with the broad concept of the present invention, some beamformer architectures may use only the initial delay and delay increments without needing to explicitly accumulate the delay. For example, a FIFO can be set to an initial length, and then lengthened by one with each delay increment by holding the read address for one clock cycle while still incrementing the write address. All such variations and modifications are intended to be encompassed by the claims set forth hereinafter.

I claim:

1. A beamforming channel comprising a signal delay device and a delay control circuit connected to said delay device for outputting a delay signal which controls the amount by which said delay device will delay a signal passing therethrough, said delay control circuit comprising:

a memory device for storing a channel-dependent parameter;

an input line for receiving beam-dependent parameters from a source external to said beamforming channel;

logic circuitry for computing initialization values and an initial delay from said channel-dependent parameter received from said memory and from said beam-dependent parameters; and delay generator circuitry for outputting signals to said delay device which cause a delay increment in response to receipt of said initialization values and said initial delay from said logic circuitry.

2. The beamformer channel as defined in claim 1, wherein said delay generator circuitry comprises state machine circuitry for applying state machine rules based on said initialization values to output delay increment signals.

3. A beamformer comprising a multiplicity of beamformer channels and a source of beam-dependent parameters connected to each of said beamformer channels, wherein each of said beamformer channels comprises a signal delay device, a memory device for storing a channel-dependent parameter and a beamforming delay processor for controlling the amount of delay produced by said signal delay device as a function of said channel-dependent parameter and said beam-dependent parameters, wherein said beamforming delay processors operate in parallel.

4. The beamformer as defined in claim 3, wherein said beamformer further comprises a summer, and said beamformer channels are receive channels connected to said summer.

5. The beamformer as defined in claim 3, wherein each of said beamformer channels is a respective transmit channel having a respective pulser associated therewith.

6. The beamformer as defined in claim 3, wherein each of said beamforming delay processors comprises:

logic circuitry for computing initialization values and an initial delay from said channel-dependent parameter received from said memory and from said beam-dependent parameters; and delay generator circuitry for outputting signals to said delay device which cause a delay increment in response to receipt of said initialization values and said initial delay from said logic circuitry.

7. The beamformer as defined in claim 3, wherein said source of beam-dependent parameters comprises a central processing unit which computes and broadcasts said beam-dependent parameters to said beamformer channels.

8. The beamformer as defined in claim 3, wherein said source of beam-dependent parameters comprises a memory from which said beam-dependent parameters are read and broadcast to said beamformer channels.

9. The beamformer as defined in claim 3, wherein said delay generator circuitry comprises state machine circuitry for applying state machine rules based on said initialization values to output delay increment signals.

10. An ultrasonic imaging system comprising a transducer array, a beamformer connected to said transducer array, a signal processor connected to said beamformer, a scan converter connected to said signal processor, a display monitor connected to said scan converter, and a source of beam-dependent parameters connected to said beamformer, wherein said transducer array comprises a multiplicity of transducer elements and said beamformer comprises a multiplicity of beamformer channels and switching circuitry for selectively coupling said beamformer channels to said transducer elements, each of said beamformer channels comprising a signal delay device, a memory device for storing a channel-dependent parameter and a beamforming delay processor for controlling the amount of delay produced by said signal delay device as a function of said channel-dependent parameters and said beam-dependent parameters, wherein said beamforming delay processors operate in parallel.

11. The ultrasound imaging system as defined in claim 10, wherein said beamformer further comprises a summer, and said beamformer channels are receive channels which couple said transducer elements to said summer.

12. The ultrasound imaging system as defined in claim 10, wherein each of said beamformer channels is a respective transmit channel having a respective pulser associated therewith, each transmit channel serving to couple a respective transducer element to a respective pulser during transmission.

13. The ultrasonic imaging system as defined in claim 10, wherein each of said beamforming delay processors comprises:

logic circuitry for computing initialization values and an initial delay from said channel-dependent parameter received from said memory and from said beam-dependent parameters; and delay generator circuitry for outputting signals to said delay device which cause a delay increment in response to receipt of said initialization values and said initial delay from said logic circuitry.

14. The ultrasound imaging system as defined in claim 10, wherein said source of beam-dependent parameters comprises a central processing unit which computes and broadcasts said beam-dependent parameters to said beamformer channels.

15. The ultrasound imaging system as defined in claim 10, wherein said source of beam-dependent parameters comprises a memory from which said beam-dependent parameters are read and broadcast to said beamformer channels.

16. The ultrasound imaging system as defined in claim 13, wherein said delay generator circuitry comprises state machine circuitry for applying state machine rules based on said initialization values to output delay increment signals.

17. A method of receive beamforming, comprising the steps of:

parallel processing dynamic delays for a plurality of receive channels using a respective state machine for each receive channel;

setting said receive channels with said respective dynamic delays;

detecting an impinging ultrasound wave using an ultrasonic transducer having a plurality of transducer elements which output a corresponding plurality of electrical signals which are not synchronized;

receiving said plurality of electrical signals in said respective plurality of receive channels set with said respective dynamic delays, said dynamic delays being computed so that said plurality of electrical signals will be synchronized after said respective dynamic delays; and summing said synchronized electrical signals to form a net electrical signal.

18. The beamforming method as defined in claim 17, further comprising the steps of broadcasting a common set of beam-dependent parameter values to each receive channel and storing respective channel-dependent parameter values in said receive channels, wherein the respective dynamic delay for each receive channel is determined as a function of said common set of beam-dependent parameter values and said respective channel-dependent parameter value.

19. A method of transmit beamforming, comprising the steps of:

parallel processing dynamic delays for a plurality of transmit channels using a respective state machine for each transmit channel;

setting said transmit channels with said respective dynamic delays;

electrically pulsing each of said transmit channels simultaneously to generate a plurality of electrical pulses;

receiving said plurality of electrical pulses in said respective plurality of transmit channels set with said respective dynamic delays, said dynamic delays being computed so that said a transducer array has a desired focal point when transducer elements thereof are excited by said plurality of delayed electrical signals.

20. The beamforming method as defined in claim 19, further comprising the steps of broadcasting a common set of beam-dependent parameter values to each transmit channel and storing respective channel-dependent parameter values in said transmit channels, wherein the respective dynamic delay for each transmit channel is determined as a function of said common set of beam-dependent parameter values and said respective channel-dependent parameter value.

* * * * *